United States Patent
Oh et al.

(10) Patent No.: US 10,209,198 B2
(45) Date of Patent: Feb. 19, 2019

(54) PARTICLE SENSING DEVICE AND AIR CONDITIONER INCLUDING THE SAME

(71) Applicant: SAMSUNG ELECTRONICS CO., LTD., Suwon-si, Gyeonggi-do (KR)

(72) Inventors: Seung Won Oh, Seongnam-si (KR); Kwon Jin Kim, Suwon-si (KR); Jin-Gyun Kim, Seongnam-si (KR); Hyeong Joon Seo, Suwon-si (KR); Sun-Hee Son, Suwon-si (KR); Woo Seog Song, Yongin-si (KR); Kang Ho Choi, Yongin-si (KR); Nak Hyun Kim, Yongin-si (KR); Young-Jae Kim, Yongin-si (KR); Ji Hong Kim, Suwon-si (KR); Hyun Ah Kim, Suwon-si (KR); Se Kwan Jeong, Osan-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 245 days.

(21) Appl. No.: 15/185,512

(22) Filed: Jun. 17, 2016

(65) Prior Publication Data
US 2016/0370301 A1    Dec. 22, 2016

(30) Foreign Application Priority Data

Jun. 19, 2015 (KR) .......... 10-2015-0087260

(51) Int. Cl.
*G01N 21/94*    (2006.01)
*G01N 21/85*    (2006.01)
(Continued)

(52) U.S. Cl.
CPC ......... *G01N 21/85* (2013.01); *G01N 15/0205* (2013.01); *G01N 2015/0046* (2013.01); *G01N 2021/8557* (2013.01)

(58) Field of Classification Search
CPC ............... G01N 15/0656; G01N 15/06; G01N 2015/0046; G01N 21/94; F01N 2560/05; F02D 41/1466
(Continued)

(56) References Cited

U.S. PATENT DOCUMENTS

| 5,072,626 A | 12/1991 | Ensor et al. |
| 5,825,487 A * | 10/1998 | Felbinger ........... G01N 15/1404 356/338 |

(Continued)

FOREIGN PATENT DOCUMENTS

| CN | 204365597 | 6/2015 |
| JP | 2015-38463 | 2/2015 |
| KR | 10-1515858 | 5/2015 |

OTHER PUBLICATIONS

Matson et al., "Measurement of Ultrafine Particles: A Comparison of Two Handheld Condensation Particle Counters", Aerosol Science and Technology, vol. 38, No. 5, Taylor and Francis Group, 2004, pp. 487-495.

(Continued)

*Primary Examiner* — Eric S McCall
*Assistant Examiner* — Mohammed E Keramet-Amircola
(74) *Attorney, Agent, or Firm* — Staas & Halsey LLP

(57) ABSTRACT

A particle sensing device and an air conditioner including a sensor has a sensing path through which air passes, a flow path housing which accommodates the sensor and guides air, and a flow path switching device to all air suctioned from the outside is guided to the sensing path, or some of the air suctioned from the outside and moving flows back in an obliquely upward direction and flows into the sensing path.

20 Claims, 11 Drawing Sheets

(51) Int. Cl.
*G01N 15/02* (2006.01)
*G01N 15/00* (2006.01)

(58) Field of Classification Search
USPC .......................................... 73/28.01
See application file for complete search history.

(56) References Cited

U.S. PATENT DOCUMENTS

| | | | |
|---|---|---|---|
| 5,932,795 A | 8/1999 | Koutrakis et al. | |
| 5,946,091 A | 8/1999 | Yufa | |
| 7,836,751 B2 | 11/2010 | Marra | |
| 2003/0142310 A1* | 7/2003 | Bedard | G01N 15/0618 |
| | | | 356/338 |
| 2004/0103785 A1* | 6/2004 | North | A47L 9/1608 |
| | | | 95/271 |
| 2004/0139785 A1* | 7/2004 | Abdul-Khalek | F02D 41/1467 |
| | | | 73/28.01 |
| 2005/0184054 A1* | 8/2005 | Kachi | H01L 21/67103 |
| | | | 219/546 |
| 2006/0283324 A1* | 12/2006 | Roques | G01N 30/6095 |
| | | | 96/101 |
| 2009/0314164 A1* | 12/2009 | Yamashita | F24F 3/1603 |
| | | | 96/245 |
| 2010/0043527 A1* | 2/2010 | Marra | B60H 1/008 |
| | | | 73/28.02 |
| 2010/0111648 A1* | 5/2010 | Tamura | H01L 21/67248 |
| | | | 414/217 |
| 2010/0243635 A1* | 9/2010 | Nakamura | F23Q 7/22 |
| | | | 219/270 |
| 2010/0288921 A1 | 11/2010 | Wang et al. | |
| 2011/0120211 A1 | 5/2011 | Bae | |
| 2011/0226675 A1 | 9/2011 | Holden et al. | |
| 2011/0265551 A1* | 11/2011 | Hopka | G01N 27/4067 |
| | | | 73/23.31 |
| 2014/0216259 A1* | 8/2014 | Iwaki | F24F 3/166 |
| | | | 96/19 |

OTHER PUBLICATIONS

International Search Report dated Sep. 12, 2016 in corresponding International Patent Application No. PCT/KR2016/006442.
European Communication dated Apr. 18, 2018 in European Patent Application No. 16811963.4.
European Search Report dated Mar. 29, 2018 in European Patent Application No. 16811963.4.

* cited by examiner

PARTICLE SENSING DEVICE AND AIR CONDITIONER INCLUDING THE SAME

CROSS-REFERENCE TO RELATED APPLICATION

This application claims benefit of foreign priority to Korean Patent Application No. 10-2015-0087260, filed on Jun. 19, 2015 in the Korean Intellectual Property Office, the disclosure of which is incorporated herein by reference.

BACKGROUND

1. Field

Embodiments of the present disclosure relate to a particle sensing device capable of measuring concentrations of fine particles and ultrafine particles and an air conditioner including the same.

2. Related Art

A particle sensing device configured to measure a concentration of particles in air is included in an air conditioner or air cleaner to be used.

The air contains fine particles having particulate matter (PM) 10 (a diameter of 10 μm or less) and ultrafine particles having PM 2.5 (a diameter of 2.5 μm or less), and it has been verified that the fine particles may influence a person's health and the ultrafine particles are particularly hazardous to a human body.

Accordingly, an air conditioner or air cleaner nowadays has a particle sensing device installed therein, and concentrations of the fine particles and the ultrafine particles can be measured by the particle sensing device.

A conventional normal particle sensing device includes a first sensor for sensing a concentration of the fine particles and a second sensor for sensing a concentration of the ultrafine particles.

SUMMARY

Therefore, it is an aspect of the present disclosure to provide a particle sensing device capable of measuring concentrations of fine particles and ultrafine particles using one sensor and an air conditioner including the same.

Additional aspects of the disclosure will be set forth in part in the description which follows and, in part, will be obvious from the description, or may be learned by practice of the disclosure.

In accordance with one aspect of the present disclosure provides a particle sensing device and an air conditioner including a sensor including a sensing path through which air passes, and a flow path housing which accommodates the sensor and guides air, wherein all air suctioned from the outside is guided to the sensing path, or some of the air suctioned from the outside and moving flows back in an obliquely upward direction and flows into the sensing path.

The sensor may include a light generator which is provided at one side of the sensing path and generates light, and a light receiver which is provided at the other side of the sensing path to face the light generator and receives the light.

The flow path housing may include a suction port through which external air is suctioned, a discharge port through which air is discharged to the outside, a first suction path which guides air to pass through the sensing path in a first direction, and a second suction path which guides air to pass through the sensing path in a second direction, and the flow path switching device selectively guides air to any one of the first suction path and the second suction path.

The flow path housing may include a bypass path which extends downward, and guides air to bypass the first suction path to be discharged through the discharge port, and the second suction path which is connected to the bypass path and extends obliquely upward with respect to the bypass path.

The flow path switching device may include a driving motor which rotates the sensor, and the sensing path is connected to any one of the first suction path and the second suction path according to rotation of the sensor.

The first direction and the second direction may form an angle of 90°, and the sensing path is connected to one of the first suction path and the suction path according to rotating the sensor by 90°.

The flow path housing includes a first discharge path connected to the sensing path with the sensing path connected to the first suction path, and a second discharge path connected to the sensing path with the sensing path connected to the second suction path.

The particle sensing device may further include a rotating housing which is rotatably installed in the flow path housing and provided with the sensor therein, wherein the rotating housing includes, a suction guide which guides air suctioned into the sensing path, a discharge guide which guides air discharged from the sensing path, a first cap which closes any one of the first suction path and the second discharge path, and a second cap which closes any one of the second suction path and the first discharge path.

The flow path housing may include a suction port through which external air is suctioned, a discharge port through which air is discharged to the outside, a first suction path which guides air toward the sensor in a first direction, a second suction path which guides air toward the sensor in a second direction, a discharge path which guides air passing through the sensing path to the discharge port, and a bypass path which guides air to the discharge port by bypassing the first suction path, wherein the flow path switching device includes a damper which selectively closes one of the first suction path and the bypass path.

The damper may include a first cap which closes the first suction path, and a second cap which closes the bypass path.

The damper may be rotatably installed in the flow path housing, and the flow path switching device includes a driving motor for rotating the damper.

The flow path housing may include a suction port through which external air is suctioned, a discharge port through which air is discharged to the outside, a main flow path which connects the suction port and the discharge port, and a sub-flow path which guides air passing through the sensing path to the discharge port, wherein the flow path switching device includes a damper which is rotatably installed in the flow path housing and guides air passing through the main flow path to pass through at least the sensing path between the discharge port and the sensing path.

The main flow path may extend in a direction perpendicular to the sensing path, and the damper includes a guide path which obliquely extends with respect to the main flow path, and guides at least some air passing through the main flow path to the sensing path, and a cap which selectively blocks air from flowing to the discharge port from the main flow path according to a rotation angle of the damper.

In accordance with another aspect of the present disclosure provides a particle sensing device and an air conditioner including a sensor including a sensing path through which air passes, a flow path housing which accommodates the sensor and guides air, and a blower unit which allows external air to pass through the sensing path and be discharged to the outside again, wherein the flow path housing includes, a suction port through which air is suctioned, a suction path which vertically extends and guides air suctioned from the outside, a guide path which is split obliquely upward from the suction path and guides air to the sensing path, a particle discharge port provided at a lower side of the suction path and configured to discharge particles, and an air discharge port through which air passing through the sensing path is discharged.

The blower unit may be allowed to suction air at a first speed and a second speed faster than the first speed.

In accordance with another aspect of the present disclosure provides a particle sensing device and an air conditioner including a sensor including a sensing path through which air passes, a first suction path which guides air including fine particles to pass through the sensing path in a first direction, and a second suction path which guides air including ultrafine particles to pass through the sensing path in a second direction different from the first direction, wherein the sensor is rotatably installed and is selectively connected to one of the first suction path and the second suction path according to a rotation angle.

The second suction path which extends downward, may be connected to a flow path which guides air to flow downward, and extends obliquely upward with respect to the flow path.

The particle sensing device may further include a driving motor which generates a rotation force and rotates the sensor.

The first direction and the second direction may form an angle of 90°, and the sensor is selectively connected to one of the first suction path and the second suction path according to rotating by 90°.

BRIEF DESCRIPTION OF THE DRAWINGS

These and/or other aspects of the disclosure will become apparent and more readily appreciated from the following description of the embodiments, taken in conjunction with the accompanying drawings of which.

DESCRIPTION OF EMBODIMENTS

Hereinafter, a particle sensing device according to a first embodiment of the present disclosure will be described in detail with reference to accompanying drawings.

Figure 1:
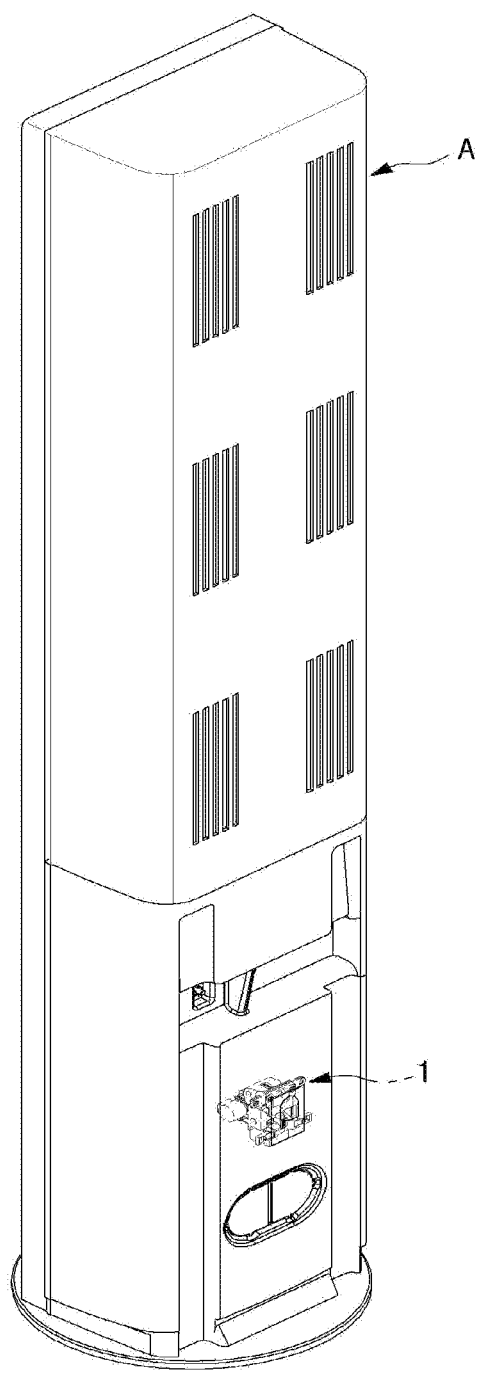
FIG. 1 is a back perspective view of an air conditioner applied with a particle sensing device according to the present disclosure.

As illustrated in FIG. 1, a particle sensing device 1 is disposed in an indoor unit A of an air conditioner so that indoor air may be suctioned and concentrations of fine particles and ultrafine particles may be measured.

Figure 2:
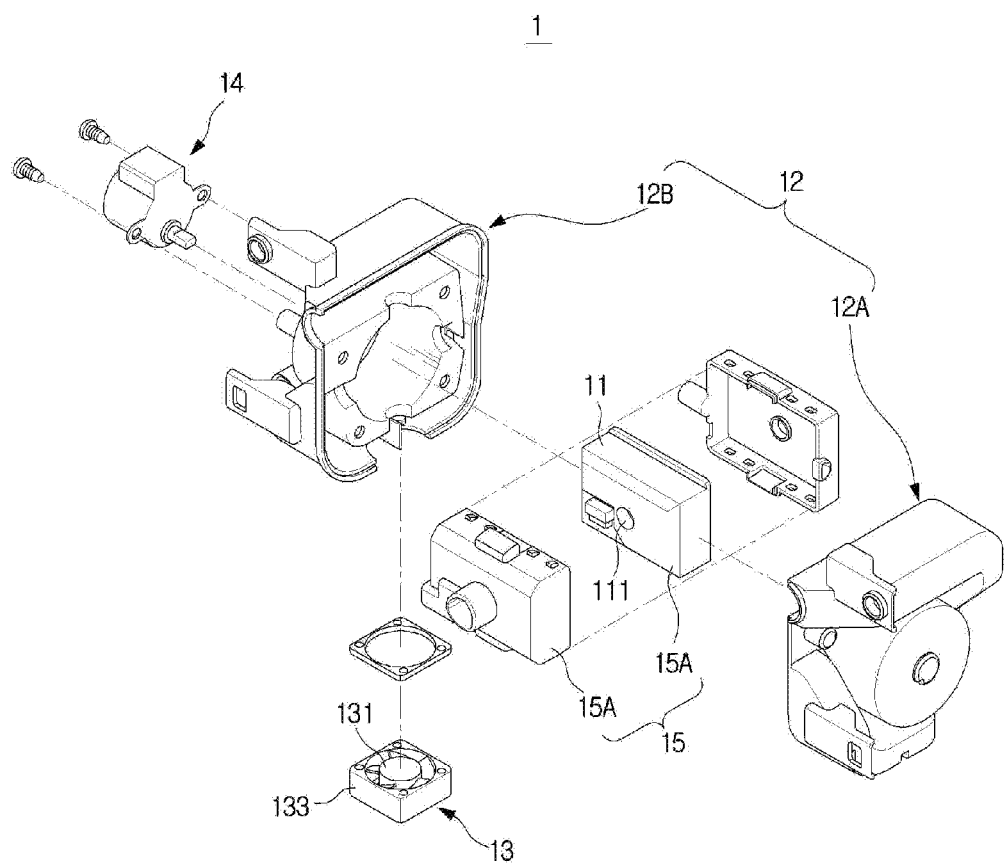
FIG. 2 is a exploded perspective view of the particle sensing device according to a first embodiment of the present disclosure.
Figure 3:
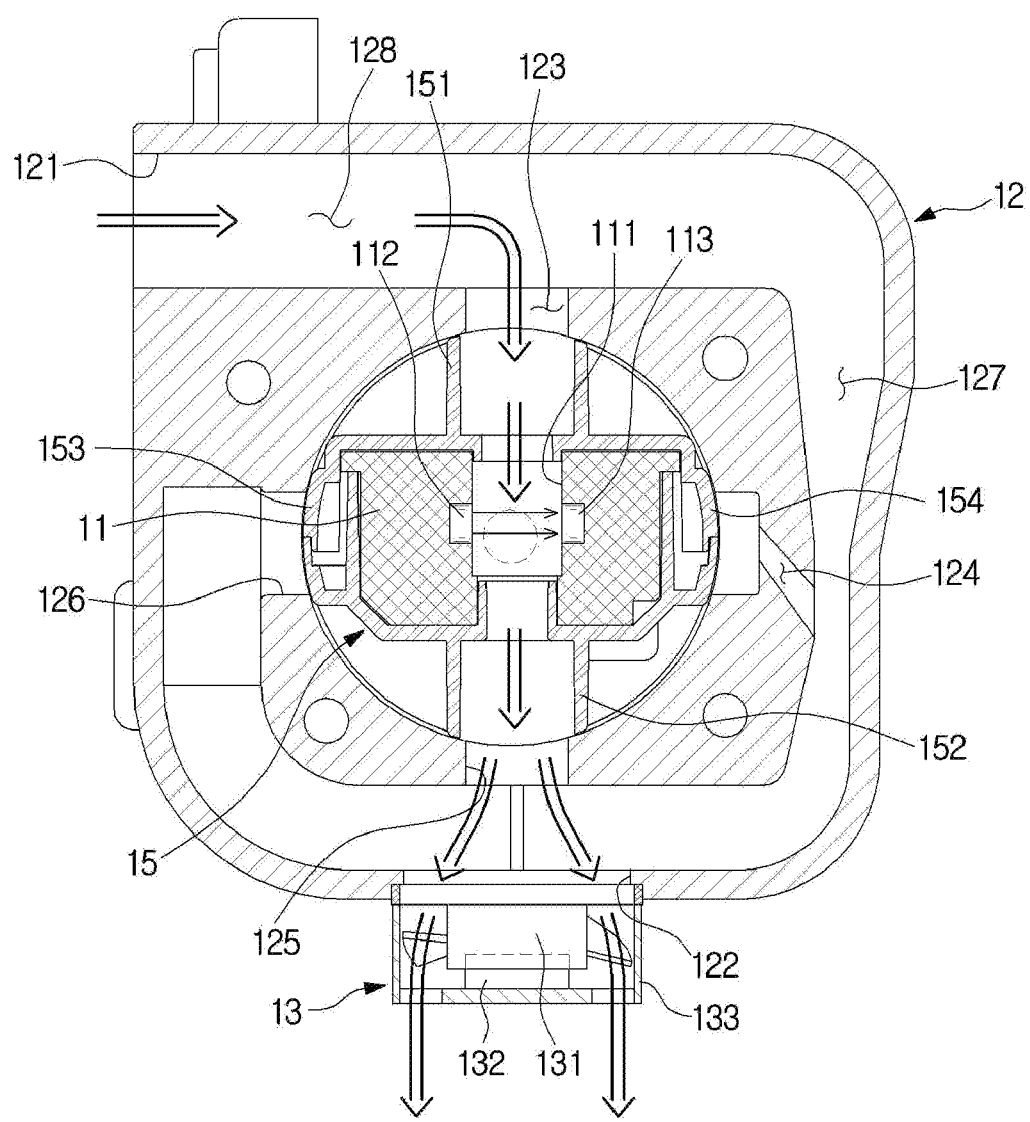
FIG. 3 and FIG. 4 are cross-section views showing motions of the particle sensing device according to the first embodiment of the present disclosure.

As illustrated in FIGS. 2 and 3, the particle sensing device 1 according to the first embodiment of the present disclosure includes a sensor 11 for sensing a concentration of particles included in air, a flow path housing 12 in which a flow path for accommodating the sensor 11 and guiding air to the sensor 11 is formed, a blower unit 13 for discharging air to the outside after external air is suctioned into the flow path housing 12 and sensed by the sensor 11, and a flow path switching device for switching the flow path provided in the flow path housing 12 and enabling fine particles and ultrafine particles to be sensed by one sensor 11.

The flow path switching device serves to transfer all air suctioned from the outside to the sensor 11, or to enable some of the air suctioned from the outside to flow back in an obliquely upward direction and the remaining air to be discharged.

When all air suctioned from the outside is transferred to the sensor 11 by the flow path switching device, since all fine particles and ultrafine particles are transferred to the sensor 11, a concentration of fine particles including the ultrafine particles is sensed by the sensor 11.

In addition, while air suctioned from the outside flows downward, when only some thereof flows obliquely upward and the remaining air flows downward to be discharged to the outside by the flow path switching device, fine particles which are relatively large move downward to be discharged to the outside, however, ultrafine particles which have a property of floating upward is transferred to the sensor 11 with some of the air flowing obliquely upward. Accordingly, a concentration of ultrafine particles is sensed by the sensor 11.

The sensor 11 includes a sensing path 111 through which air passes to be sensed, a light generator 112 which is disposed at one side of the sensing path 111 and generates light, and a light receiver 113 which is disposed at the other side of the sensing path 111 to face the light generator 112 and receives light generated by the light generator 112. Accordingly, with the light generator 112 generating light and an amount of light received by the light receiver 113 being measured, a concentration of fine particles or ultrafine particles included in air passing through the sensing path 111 is measured.

The flow path housing 12 is formed by a pair of flow path housings 12A and 12B coupled to each other and includes a suction port 121 through which external air is suctioned, an discharge port 122 through which air is discharged to the outside, a first suction path 123 which guides all air suctioned from the outside to the sensor 11, a second suction path 124 through which only some air suctioned from the outside is transferred to the sensor 11, a bypass path 127 through which air bypasses the first suction path 123 to be transferred to the discharge port 122, a first discharge path 125 which is connected to one side of the sensing path 111 with the other side of the sensing path 111 connected to the first suction path 123 and guides air passing through the sensing path 111 to the discharge port 122, and a second discharge path 126 which is connected to one side of sensing path 111 with the other side of the sensing path 111 connected to the second suction path 124 and guides air passing through the sensing path 111 to the discharge port 122. In addition, the flow path housing 12 includes a main suction path 128 which guides air suctioned from the suction port 121 to the first suction path 123 and the bypass path 127.

The bypass path 127 extends downward to guide air downward, and the second suction path 124 connected to the bypass path 127 extends obliquely upward with respect to the bypass path 127 which guides air downward to enable some of the air passing through the bypass path 127 to flow obliquely upward.

The first suction path 123 and the first discharge path 125 guide air to pass through the sensing path 111 in a first direction, the second suction path 124 and the second discharge path 126 guide air to pass through the sensing path 111 in a second direction. In the embodiment, the first direction and the second direction form an angle of 90°.

In the embodiment, the flow path switching device includes a driving motor 14 which generates a rotational force to rotate the sensor 11. In the embodiment, the driving motor 14 includes a stepping motor configured to precisely control a rotation angle of the sensor 11, and the sensing path 111 provided in the sensor 11 is connected to the first suction path and the first discharge path 125 or to the second suction path 124 and the second discharge path 126 as the driving motor 14 rotates the sensor 11 by 90°.

The flow path housing 12 includes a rotating housing 15 which accommodates the sensor 11 and is rotatably installed in the flow path housing 12, and thus, the sensor 11 is rotatably installed in the flow path housing 12 using the rotating housing 15.

The rotating housing 15 is formed by a pair of rotating housings 15A and 15B which are mutually coupled from both sides of the sensor 11 and includes a first guide 151 which guides air transferred through the first suction path 123 to the sensing path 111 or air passing through the sensing path 111 to the second discharge path 126 and a second guide 152 which guides air transferred through the second suction path 124 to the sensing path 111 or guides air passing through the sensing path 111 to the first discharge path 125.

In addition, the rotating housing 15 includes a first cap 153 which closes any one of the first suction path 123 and the second discharge path 126 depending on the rotation angle of the rotating housing 15 and a second cap 154 which closes any one of the second suction path 124 and the first discharge path 125 depending on the rotation angle of the rotating housing 15.

The blower unit 13 is coupled to the above-described discharge port 122 and includes a blower fan 131 which includes an axial-flow fan to suction air from the direction of the flow path housing 12 through the discharge port 122 and discharges the air to the outside, a blower motor 132 which rotates the blower fan 131, and a blower frame 133 which forms a flow path through which air flows and supports the blower motor 132.

Next, an operation of the particle sensing device 1 formed as described above will be described with reference to the drawings.

First, as illustrated in FIG. 3, by rotating the rotating housing 15 and the sensor 11 using the driving motor 14, the sensing path 111 is connected to the first suction path 123 and the first discharge path 125, and the second suction path 124 and the second discharge path 126 are respectively closed by the first cap 153 and the second cap 154.

In the above state, when the blower unit 13 is operated, external air is suctioned into the flow path housing 12 through the suction port 121 by a suction force generated by the blower unit 13, sequentially passes through the first suction path 123, the sensing path 111, and the first discharge path 125, and is fully discharged through the discharge port 122.

At this point, since all of the air suctioned from the outside is transferred to the sensing path 111, the sensor 11 senses concentrations of fine particles and ultrafine particles included in air passing through the sensing path 111.

Figure 4:
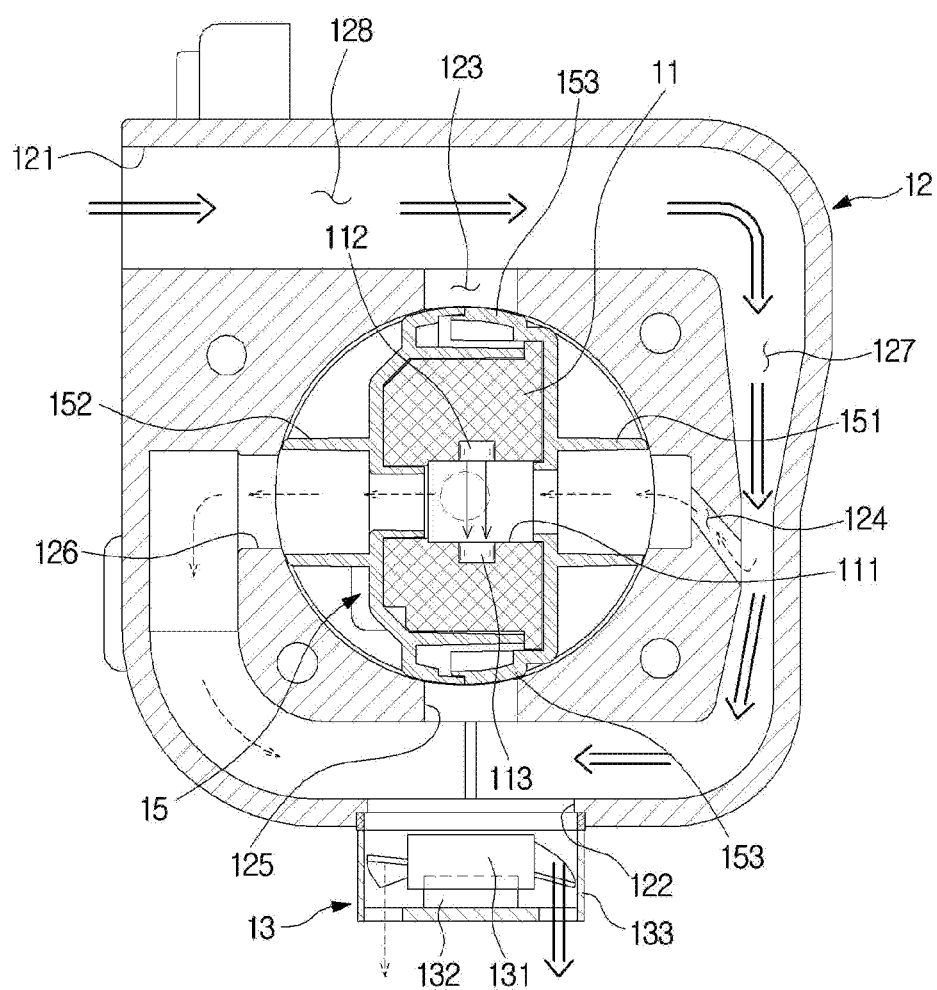

Next, as illustrated in FIG. 4, by rotating the rotating housing 15 and the sensor 11 using the driving motor 14, the sensing path 111 is connected to the second suction path 124 and the second discharge path 126, and the second suction path 124 and the first discharge path 125 are respectively closed by the first cap 153 and the second cap 154.

In the above state, when the blower unit 13 is operated, external air is suctioned into the flow path housing through the suction port 121 by a suction force generated by the blower unit 13 and is discharged through the discharge port 122 via the bypass path 127.

In a process in which air passes through the bypass path 127 and flows downward, some of the air passing through the bypass path 127 flows back in an obliquely upward direction through the second suction path 124, is transferred to the sensing path 111, and is discharged through the discharge port 122 via the second discharge path 126, and all remaining air is discharged through the discharge port 122 via the bypass path 127.

At this point, all fine particles heavier than ultrafine particles are discharged through the discharge port 122 with air discharged through discharge port 122, however, since the ultrafine particles have a property of floating upward due to low weight, the ultrafine particles are included in air flowing obliquely upward through the second suction path 124 and pass through the sensing path 111. Since only the ultrafine particles are transferred through the second suction path 124, the sensor 11 senses a concentration of only ultrafine particles included in air passing through the sensing path 111.

Hereinafter, a particle sensing device according to a second embodiment of the present disclosure will be described in detail with reference to the drawings.

Figure 5:
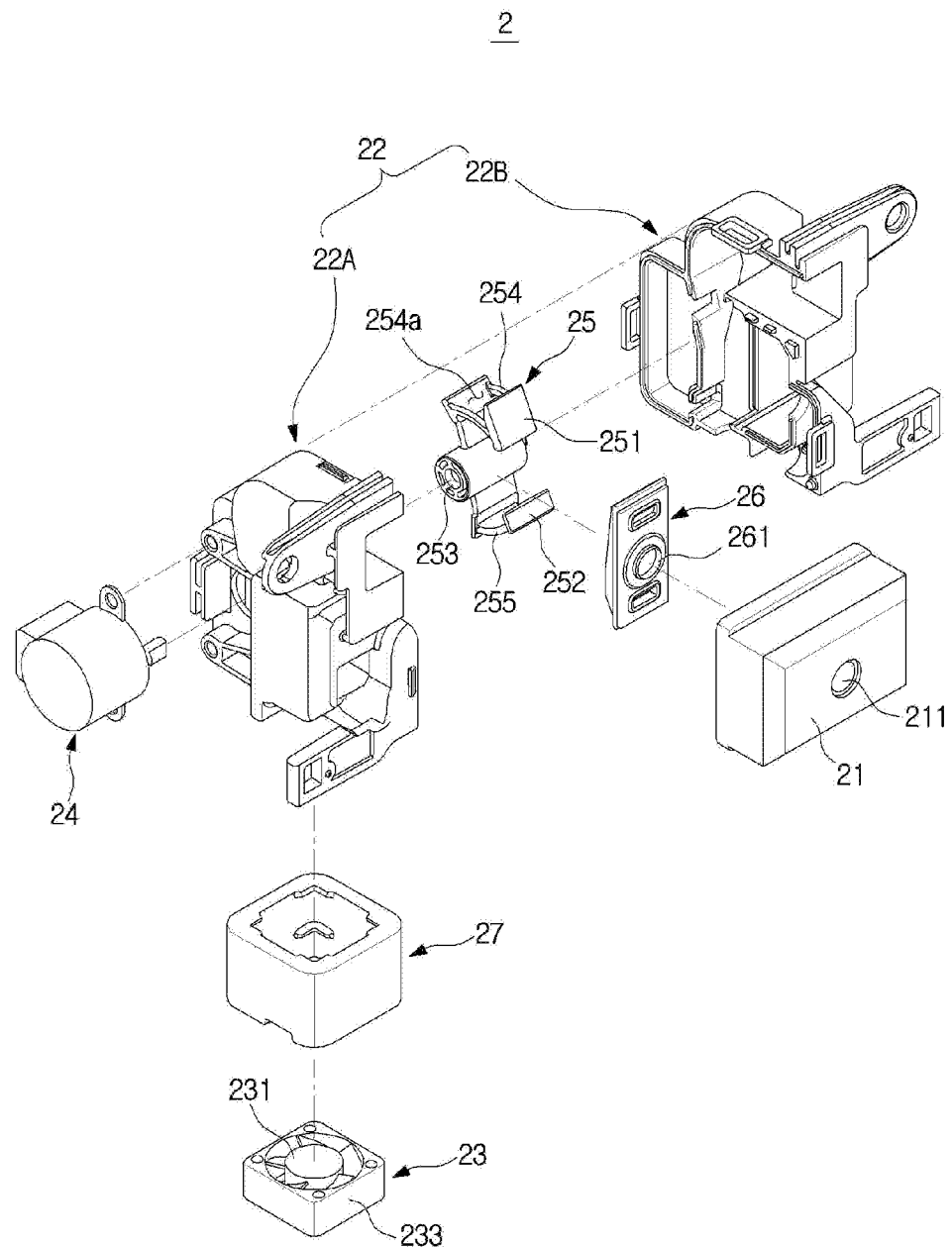
FIG. 5 is a exploded perspective view of the particle sensing device according to a second embodiment of the present disclosure.
Figure 6:
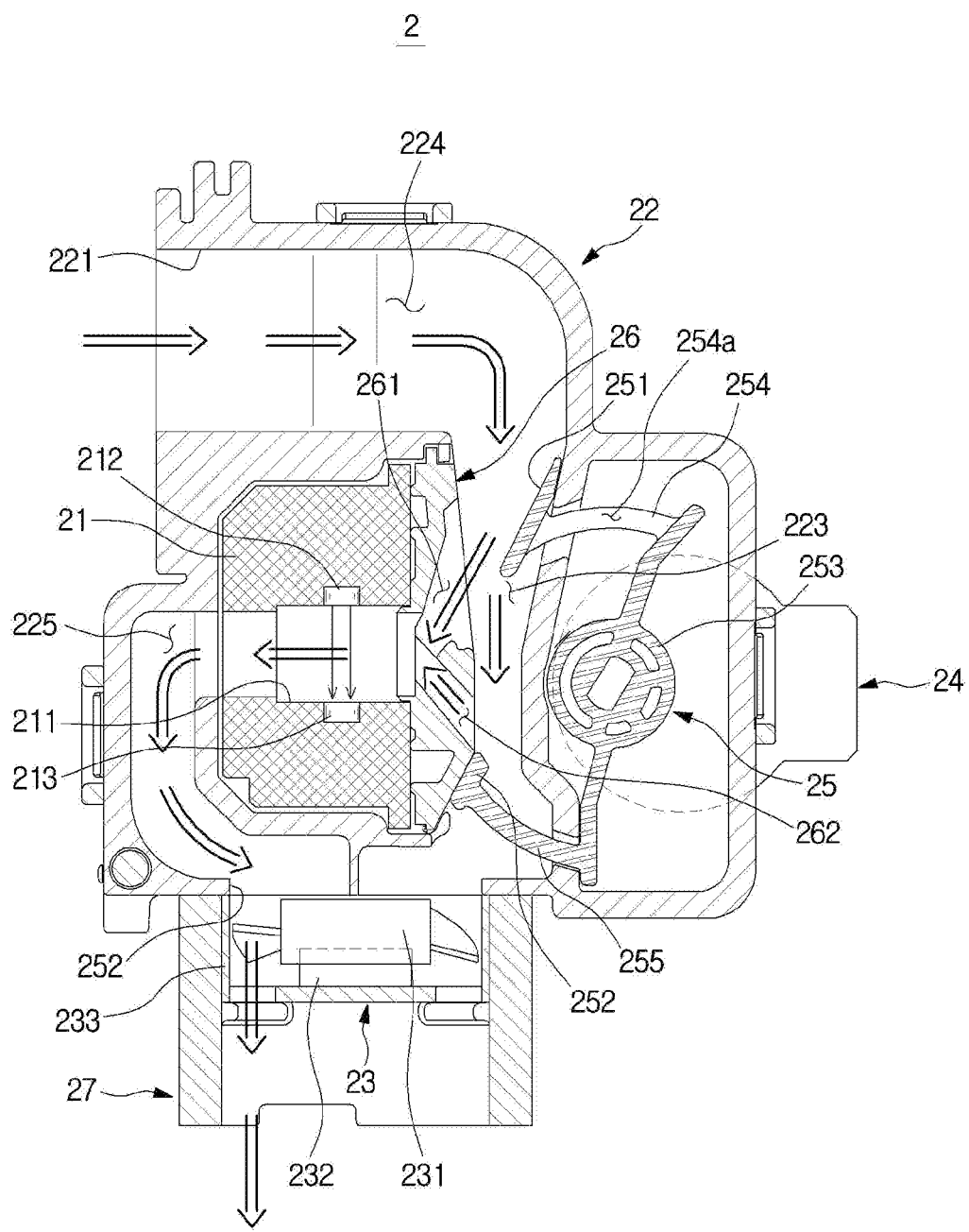
FIG. 6 and FIG. 7 are cross-section views showing motions of a particle sensing device according to the second embodiment of the present disclosure.

As illustrated in FIG. 5 and FIG. 6, a particle sensing device 2 according to the second embodiment of the present disclosure includes a sensor 21 which senses a concentration of particles included in air, a flow path housing 22 in which a flow path configured to accommodate the sensor 21 and guide air to the sensor 21 is formed, a blower unit 23 which discharges air to the outside again after external air is suctioned through the flow path housing 22 and sensed by the sensor 21, and a flow path switching device which switches a flow path provided in the flow path housing 22 and enables one sensor 21 to sense both fine particles and ultrafine particles.

The sensor 21 includes a sensing path 211 through which air passes to be sensed, a light generator 212 which is disposed at one side of the sensing path 211 and generates light, and a light receiver 213 which is disposed at the other side of the sensing path 211 to face the light generator 212 and receives light generated by the light generator 212.

The flow path housing 22 is formed by a pair of flow path housings 22A and 22B coupled to each other and includes a suction port 221 through which external air is suctioned, a discharge port 222 through which air is discharged to the outside, a first suction path 261 which guides all air suctioned from the outside to the sensor 21, a second suction path 262 through which some of the air suctioned from the outside is transferred to the sensor 21, a discharge path 225 which guides air passing through the sensing path 211 to the discharge port 222, a bypass path 223 which guides air to bypass the first suction path 261 and guides air to the discharge port 222, and a main suction path 224 which guides air suctioned through the suction port 221 to the first suction path 261 and the bypass path 223.

The bypass path 223 extends downward to guide air downward, and the first suction path 261 extends obliquely downward with respect to the bypass path 223. In addition, the second suction path 262 extends obliquely upward with respect to the bypass path 223. In the embodiment, the first suction path 261 and the second suction path 262 are provided in a flow path forming member 26 disposed in the flow path housing 22.

The flow path switching device includes a driving motor 24 and a damper 25 which is rotated by the driving motor 24 and selectively closes any one of the first suction path 261 and the bypass path 223.

The damper 25 includes a first cap 251 which closes the first suction path 261, a second cap 252 which is supported by the flow path forming member 26 and closes a downstream side of the bypass path 223, a hinge 253 which is connected to a shaft of the driving motor 24 to form a rotational center of the damper 25, a first female 254 which connects the hinge 253 and the first cap 251, and a second female 255 which connects the hinge 253 and the second cap 252 and closes the bypass path 223 with the second cap 252. The first female 254 is provided with a through hole 254a which enables air to pass through the first female 254 to flow even when the first suction path 261 is closed by the first cap 251.

The blower unit 23 is coupled to the above-described discharge port 222 and includes a blower fan 231 which includes an axial-flow fan to suction air from the direction of the flow path housing 22 through the discharge port 222 and discharges the air to the outside, a blower motor 232 which rotates the blower fan 231, and a blower frame 233 which forms a flow path through which air flows and supports the blower motor 232.

A discharge guide 27 in a pipe shape which guides air discharged through the discharge port 222 is installed in the discharge port 222, and the blower unit 23 is installed in the discharge guide 27.

Next, an operation of the particle sensing device 2 formed as described above will be described with reference to the drawings.

First, as illustrated in FIG. 6, the first suction path 261 is opened by rotating the damper 25 using the driving motor 24, and the bypass path 223 is closed by the second cap 252 and the second female 255.

In the above state, when the blower unit 23 is operated, external air is suctioned into the flow path housing 22 through the suction port 221 by a suction force generated by the blower unit 23, sequentially passes through the main suction path 224, the sensing path 211, and the discharge path 225, and is fully discharged to the outside through the discharge port 222.

At this point, since all of the air suctioned from the outside is transferred to the sensing path 211, the sensor 21 senses concentrations of fine particles and ultrafine particles included in air passing through the sensing path 211.

Figure 7:
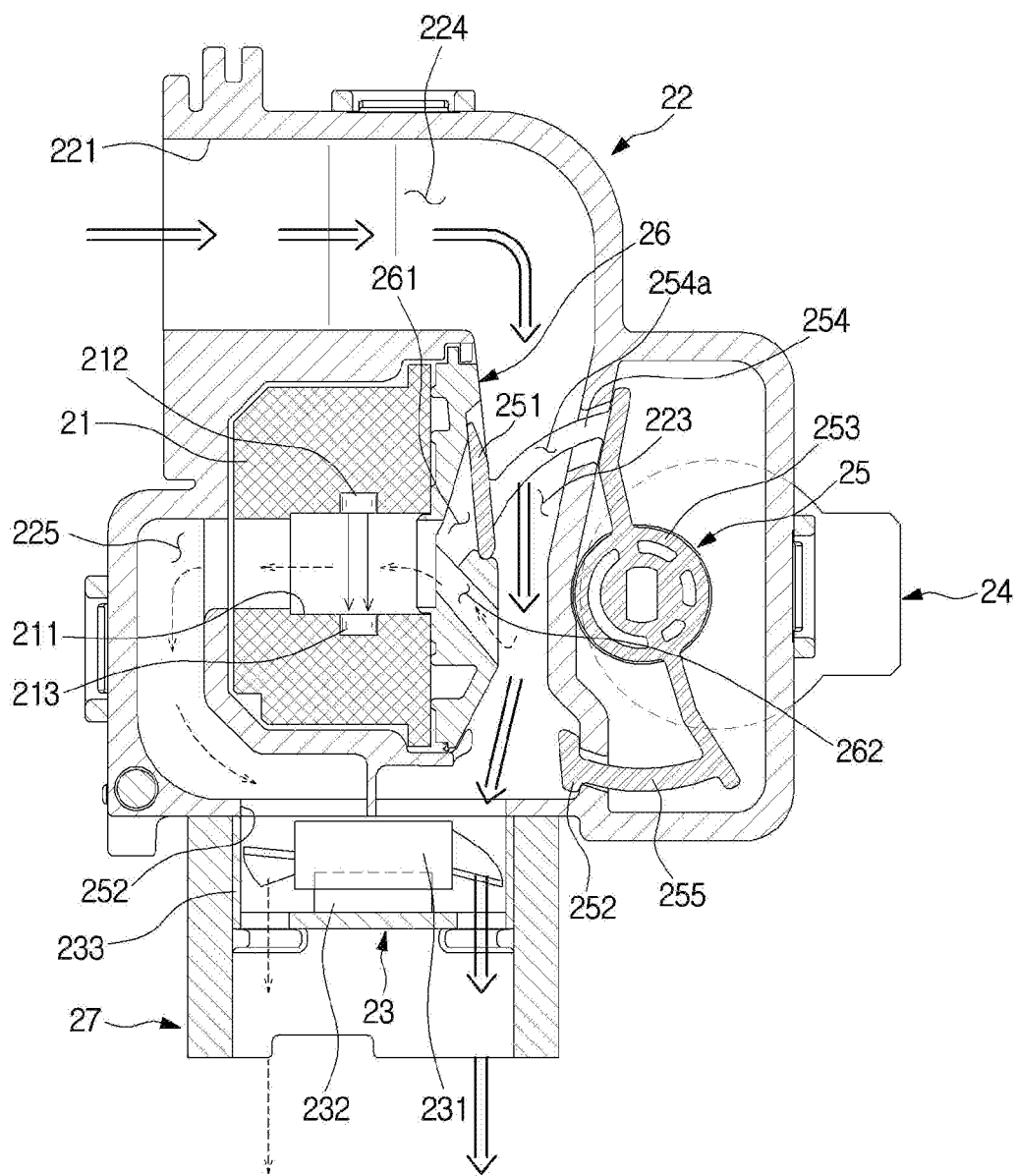

Next, as illustrated in FIG. 7, the bypass path 223 is opened by rotating the damper 25 using the driving motor 24, and the first suction path 261 is closed by the first cap 251.

In the above state, when the blower unit 23 is operated, external air is suctioned into the flow path housing 22 through the suction port 221 by a suction force generated by the blower unit 23, passes through the main suction path 224 and the bypass path 223, and is discharged to the outside through the discharge port 222.

In a process in which air passes through the bypass path 223 and flows downward, some of the air flows back in an obliquely upward direction through the second suction path 262, is transferred to the sensing path 211, and is discharged through the discharge port 222 via the discharge path 225, and all remaining air is discharged through the discharge port 222 via the bypass path 223.

At this point, fine particles which are heavier than ultrafine particles are discharged through the discharge port 222 intact with air discharged through the discharge port 222, however, since the ultrafine particles have a property of floating upward due to low weight, the ultrafine particles are included in air flowing obliquely upward through the second suction path 262 and pass through the sensing path 211. Since only the ultrafine particles are transferred through the second suction path 262, the sensor 21 senses a concentration of only ultrafine particles included in air passing through the sensing path 211.

Hereinafter, a particle sensing device according to a third embodiment of the present disclosure will be described in detail with reference to the drawings.

Figure 8:
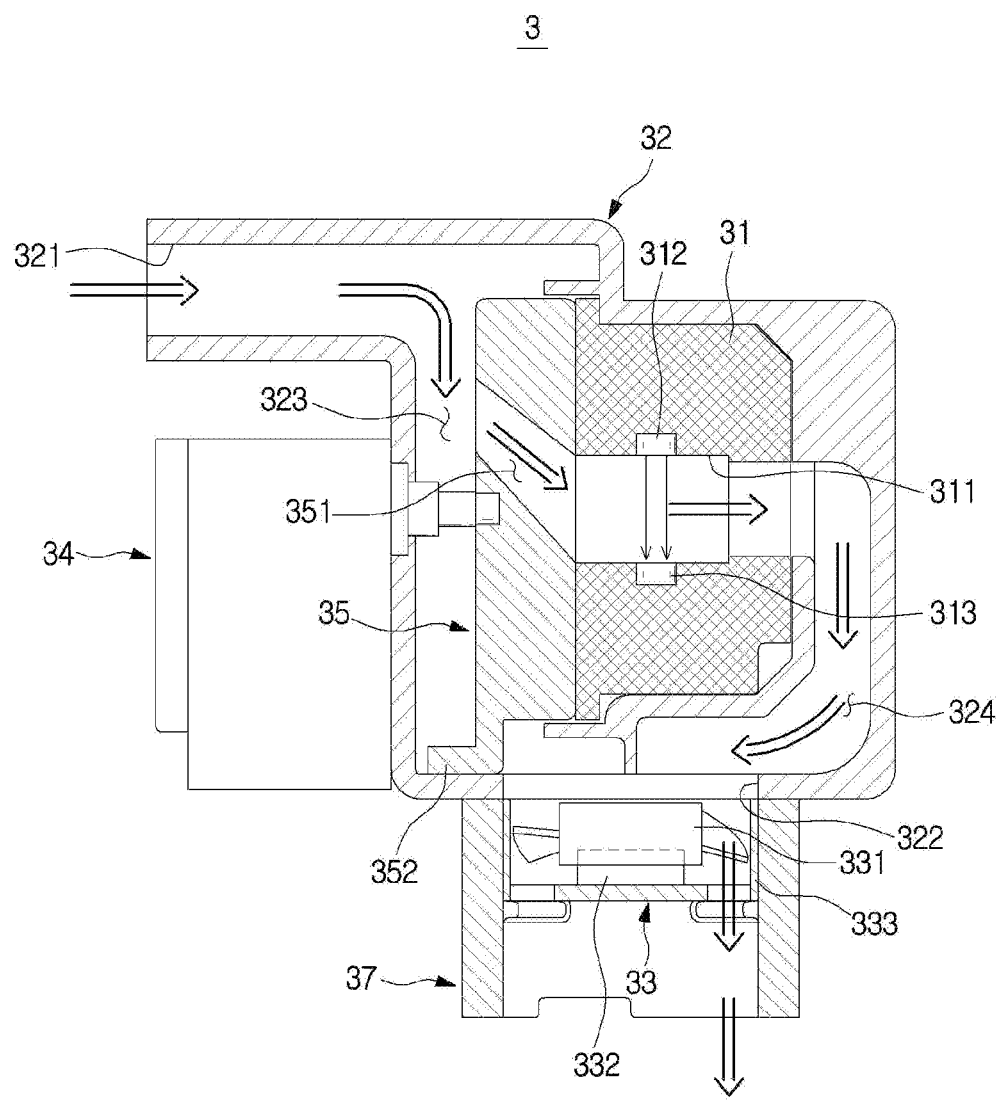
FIG. 8 and FIG. 9 are cross-section views showing motions of a particle sensing device according to a third embodiment of the present disclosure.

As illustrated in FIG. 8, a particle sensing device 3 according to the third embodiment of the present disclosure includes a sensor 31 which senses a concentration of particles included in air, a flow path housing 32 in which a flow path configured to accommodate the sensor 31 and guide air to the sensor 31 is formed, a blower unit 33 which discharges air to the outside again after external air is suctioned through the flow path housing 32 and sensed by the sensor 31 and a flow path switching device which switches a flow path provided in the flow path housing 32 and enables one sensor 31 to sense both fine particles and ultrafine particles.

The sensor 31 includes a sensing path 311 through which air passes to be sensed, a light generator 312 which is disposed at one side of the sensing path 311 and generates light, and a light receiver 313 which is disposed at the other side of the sensing path 311 to face the light generator 312 and receives light generated by the light generator 312.

The flow path housing 32 includes a suction port 321 through which external air is suctioned, an discharge port 322 through which air is discharged, a main flow path 323 which connects the suction port 321 and the discharge port 322, and transfers all air suctioned through the suction port 321 to the discharge port 322, and a sub-flow path 324 which guides air passing through the sensing path 311 provided in the sensor 31 to the discharge port 322. The main flow path 323 is vertically provided and guides air suctioned through the suction port 321 downward, the sensing path 311 is horizontally provided, and thus, the main flow path 323 and the sensing path 311 are provided perpendicular to each other.

The flow path switching device includes a driving motor 34 and a damper 35 which is rotatably installed in the flow path housing 32 and guides air passing through the main flow path 323 to be always transferred to at least the sensing path 311 between the discharge port 322 and the sensing path 311, and the damper 35 receives a rotational force from the driving motor to rotate.

The damper 35 includes a guide path 351 which obliquely extends with respect to the main flow path 323 extending obliquely downward and guides at least some air flowing downward along the main flow path 323 to flow into the sensing path 311, a cap 352 which selectively blocks air from flowing to the damper 35 from the main flow path 323 depending on the rotation angle of the discharge port 322.

Accordingly, as the damper 35 rotates by 180°, the guide path 351 provided in the damper 35 becomes inclined downward with respect to the main flow path 323 or becomes inclined upward. The cap 352 blocks air transferred from the main flow path 323 to the discharge port 322 from flowing in a state in which the cap 352 is inclined downward with respect to air passing through the main flow path 323.

The blower unit 33 is coupled to the above-described discharge port 322 and includes a blower fan 331 which includes an axial-flow fan to suction air from the direction of the flow path housing 32 through the discharge port 322 and discharges the air to the outside, a blower motor 332 which rotates the blower fan 331, and a blower frame 333 which forms a flow path through which air flows, and supports the blower motor 332.

A discharge guide 37 in a pipe shape which guides air discharged through the discharge port 322 is installed in the discharge port 322, and the blower unit 33 is installed in the discharge guide 37.

Next, an operation of the particle sensing device 3 formed as described above will be described with reference to the drawings.

First, as illustrated in FIG. 8, by rotating the damper 35 using the driving motor 44, the guide path 351 is disposed obliquely downward with respect to the main flow path 323, and the cap 352 blocks air transferred from the main flow path 323 to the discharge port 322 from flowing.

In the above state, when the blower unit 33 is operated, external air is suctioned into the flow path housing 32 through the suction port 321 by a suction force generated by the blower unit 33, sequentially passes through the main flow path 323, the guide path 351, the sensing path 311, and the sub-flow path 324, and is fully discharged to the outside through the discharge port 322.

At this point, since all of the air suctioned from the outside is transferred to the sensing path 311, the sensor 31 senses concentrations of fine particles and ultrafine particles included in air passing through the sensing path 311.

Figure 9:
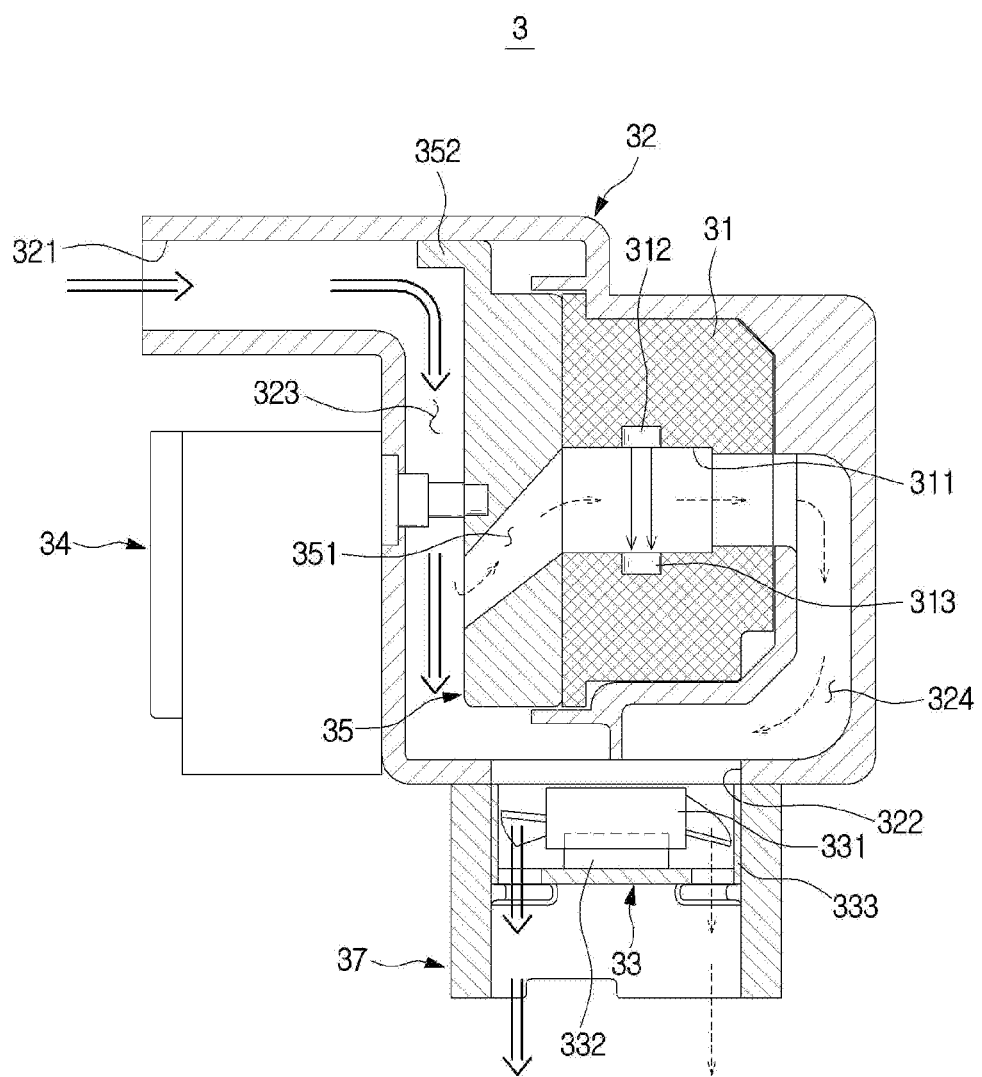

Next, as illustrated in FIG. 9, by rotating the damper 25 using the driving motor 24, the guide path 351 is disposed obliquely upward with respect to the main flow path 323, and the cap 352 does not block air transferred from the main flow path 323 to the discharge port 322 from flowing any more.

In the above state, when the blower unit 33 is operated, external air is suctioned into the flow path housing 32 through the suction port 321 by a suction force generated by the blower unit 33, passes through the main flow path 323, and is discharged to the outside through the discharge port 322.

In a process in which air passes through the main flow path 323, some of the air flows back in an obliquely upward direction through the guide path 351, is transferred to the sensing path 311, and is discharged through the discharge port 322 via the sub-flow path 324, and all remaining air is discharged through the discharge port 322 via the main flow path 323

At this point, all fine particles heavier than ultrafine particles are discharged through the discharge port 322 with air discharged through the discharge port 322, however, since the ultrafine particles have a property of floating due to low weight, the ultrafine particles are included in air flowing obliquely upward through guide path 351 and pass through the sensing path 311. Accordingly, since only the ultrafine particles are transferred through the second suction path 324, the sensor 31 senses a concentration of only ultrafine particles included in air passing through the sensing path 311.

Hereinafter, a particle sensing device according to a fourth embodiment of the present disclosure will be described in detail with reference to the drawings.

Figure 10:
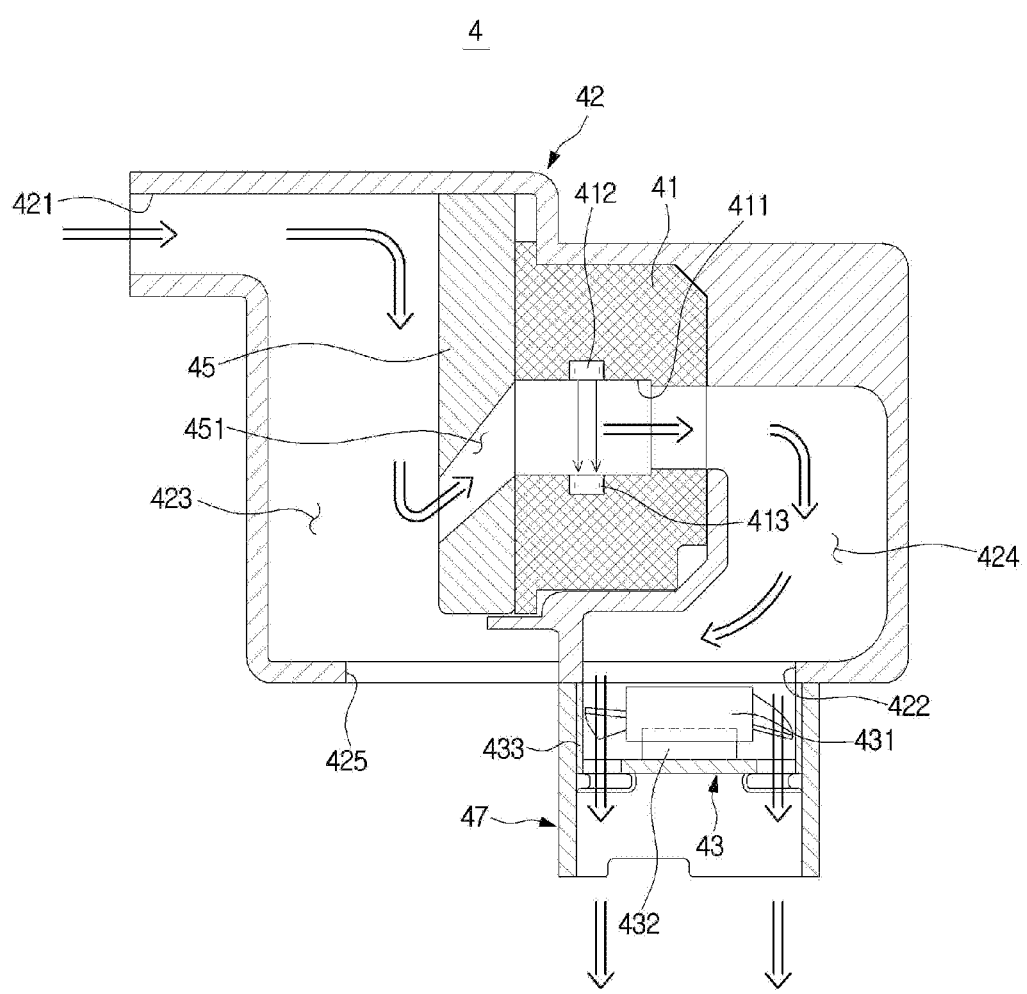
FIG. 10 and FIG. 11 are cross-section views showing motions of a particle sensing device according to the a fourth embodiment of the present disclosure.

As illustrated in FIG. 10, a particle sensing device 4 according to the fourth embodiment of the present disclosure includes a sensor 41 which senses a concentration of particles included in air, a flow path housing 42 in which a flow path configured to accommodate the sensor 41 and guide air to the sensor 41 is formed, and a blower unit 43 which discharges air to the outside again after external air is suctioned through the flow path housing 42 and sensed by the sensor 41.

The sensor 41 includes a sensing path 411 through which air passes to be sensed, a light generator 412 which is disposed at one side of the sensing path 411 and generates light, and a light receiver 413 which is disposed at the other side of the sensing path 411 to face the light generator 412 and receives light generated by the light generator 412.

The flow path housing 42 includes a suction port 421 through which air is suctioned, an air discharge port 422 through which air passing through the sensing path 411 is discharged, a suction path 423 which vertically extends and guides air suctioned from the outside, a guide path 451 which is split obliquely upward from the suction path 423 and guides air to the sensing path 411, a particle discharge port 425 provided at a lower side of the suction path 423 to discharge particles, and a discharge path 424 which guides air passing through the sensing path 411 to the air discharge port 422. In the embodiment, the guide path 451 is provided in the flow path forming member 45 installed in the flow path housing 42.

The blower unit 43 is coupled to the above-described air discharge port 422 and includes a blower fan 431 which includes an axial-flow fan to suction air from a side of the flow path housing 42 through the air discharge port 422 and discharges the air to the outside, a blower motor 432 which rotates the blower fan 431, and a blower frame 433 which forms a flow path through which air flows and supports the blower motor 432. In the embodiment, the blower unit 43 may adjust a rotational speed of the blower fan 431 such that the blower unit 43 suctions air with a first speed, and a second speed faster than the first speed.

When the blower unit 43 suctions air at the first speed, since a suction force applied from a side of the guide path 451 is small, fine particles included in air passing through the suction path 423 fall downward due to gravity and are discharged through the particle discharge port 425.

On the contrary, ultrafine particles having weights lighter than that of the fine particles are suctioned into the guide path 451 with air by a suction force applied from the side of the guide path 451, pass through the sensing path 411 and the discharge path 424, and are discharged through the air discharge port 422.

Accordingly, the sensor 41 senses a concentration of ultrafine particles included in air passing the sensing path 411.

Figure 11:
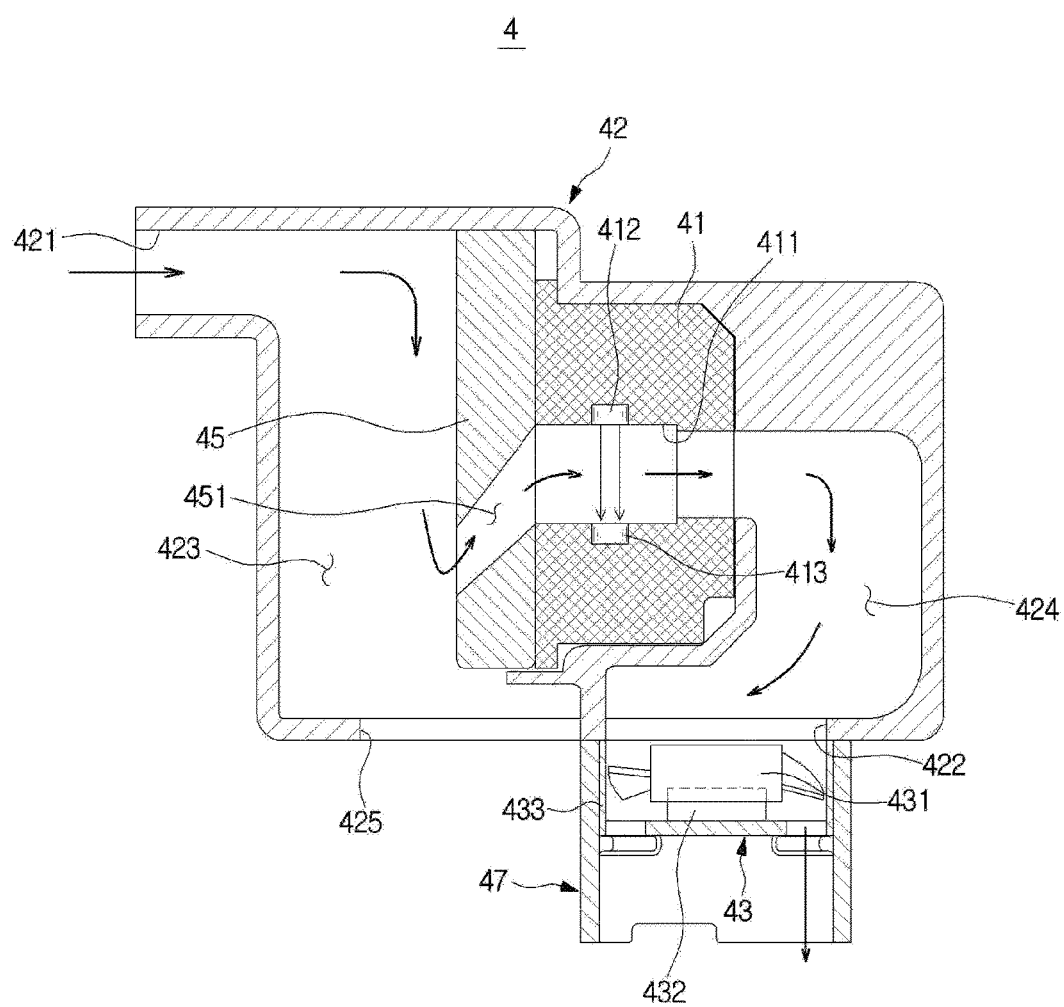

In addition, as illustrated in FIG. 11, when the blower unit 43 suctions air at the second speed faster than the first speed, since a suction force applied from the side of the guide path 451 is great and all of the fine particles and ultrafine particles are suctioned into the guide path 451, air including the fine particles and ultrafine particles is transferred to the sensing path 411.

Accordingly, the sensor 41 senses concentrations of fine particles and ultrafine particles included in air passing through the sensing path 411.

As is apparent from the above description, a particle sensing device and an air conditioner including the same according to one embodiment of the present disclosure can measure concentrations of fine particles and ultrafine particles using one sensor because all air is transferred to a sensor or some air flows back in an obliquely upward direction and is transferred to a sensor through a flow path switching device.

The present disclosure is not limited to the above-described embodiments, and it is clear to those skilled in the art that various modifications and alterations may be made therein without departing from the spirit and scope of the present disclosure. Accordingly, modified or altered embodiments fall within the scope of the appended claims.

What is claimed is:

1. A particle sensing device comprising:
a sensor including a sensing path through which air passes; and
a flow path housing which accommodates the sensor and guides air suctioned into the flow path housing from an outside, wherein
in a first operational state of the particle sensing device, all of the air suctioned from the outside is guided to the sensing path, and
in a second operational state of the particle sensing device, only a portion of the air suctioned from the outside flows into the sensing path, after changing flow direction inside the flow path housing to flow in an obliquely upward direction to reach the sensing path.

2. The particle sensing device of claim 1, wherein the sensor includes:
a light generator, provided at one side of the sensing path, to generate light; and
a light receiver, provided at another side of the sensing path so as to face the light generator, to receive the light.

3. The particle sensing device of claim 1, wherein the flow path housing includes:
a suction port through which external air is suctioned into the flow path housing;
a discharge port through which air is discharged to the outside;
a first suction path which guides air into the sensing path in a first direction when connected to the sensing path; and
a second suction path which guides air into the sensing path in a second direction when connected to the sensing path,
the particle sensing device further comprises a flow path switching device that selectively guides air to the sensing path from any one of the first suction path and the second suction path, by selectively connecting the sensing path to the any one of the first suction path and the second suction path, and
the flow path switching device connects the sensing path to the first and second suction paths to implement the first operational state and the second operational state, respectively.

4. The particle sensing device of claim 3, wherein
the flow path housing includes a bypass path which extends downward, and guides air to bypass the first suction path to be discharged through the discharge port, and
the second suction path is connected to the bypass path and extends obliquely upward with respect to the bypass path.

5. The particle sensing device of claim 3, wherein
the flow path switching device includes a driving motor to rotate the sensor, and
the sensing path is connected to any one of the first suction path and the second suction path according to a rotational position of the sensor.

6. The particle sensing device of claim 5, wherein
the first direction and the second direction form an angle of about 90°, and
rotation of the sensor by about 90° causes a suction path connected to the sensing path to change from one of the first suction path and the suction path to another of the first and second suction paths.

7. The particle sensing device of claim 5, wherein the flow path housing further includes:
a first discharge path connected to the sensing path when the sensing path is connected to the first suction path; and
a second discharge path connected to the sensing path when the sensing path is connected to the second suction path.

8. The particle sensing device of claim 7, further comprising:
a rotating housing rotatably installed in the flow path housing, provided with the sensor therein, and including:
a suction guide which guides air suctioned into the sensing path;
a discharge guide which guides air discharged from the sensing path;
a first cap which closes any one of the first suction path and the second discharge path; and
a second cap which closes any one of the second suction path and the first discharge path.

9. The particle sensing device of claim 1, wherein the flow path housing includes:
a suction port through which external air is suctioned into the flow path housing;
a discharge port through which air is discharged to the outside;
a first suction path which guides air toward the sensor in a first direction;
a second suction path which guides air toward the sensor in a second direction;
a discharge path which guides air passing through the sensing path to the discharge port; and
a bypass path which guides air to the discharge port by bypassing the first suction path,
the particle sensing device further comprises a flow path switching device including a damper which selectively closes one of the first suction path and the bypass path, and
the damper closes the bypass path and the first suction path to implement the first operational state and the second operational state, respectively.

10. The particle sensing device of claim 9, wherein the damper includes:
a first cap which closes the first suction path; and
a second cap which closes the bypass path.

11. The particle sensing device of claim 9, wherein
the damper is rotatably installed in the flow path housing, and
the flow path switching device includes a driving motor to rotate the damper.

12. The particle sensing device of claim 1, wherein the flow path housing includes:
a suction port through which external air is suctioned into the flow path housing;

a discharge port through which air is discharged to the outside;

a main flow path which connects the suction port and the discharge port; and a sub-flow path which guides air passing through the sensing path to the discharge port, and the particle sensing device further comprises a flow path switching device including a damper which is rotatably installed in the flow path housing and guides air passing through the main flow path to pass through at least the sensing path between the discharge port and the sensing path.

13. The particle sensing device of claim 12, wherein the main flow path extends in a direction perpendicular to the sensing path, the damper includes:

a guide path which obliquely extends with respect to the main flow path, and guides at least some air passing through the main flow path to the sensing path; and a cap which selectively blocks air from flowing to the discharge port from the main flow path according to a rotation angle of the damper, and the cap selectively blocks and permits air from flowing to the discharge port from the main flow path to implement the first operational state and the second operational state, respectively.

14. An air conditioner comprising the particle sensing device of claim 1.

15. A particle sensing device comprising:

a sensor including a sensing path through which air passes;

a flow path housing which accommodates the sensor and guides air; and a blower unit which causes external air to pass through the sensing path and be discharged to the outside, wherein the flow path housing includes:

a suction port through which air is suctioned;

a suction path which vertically extends and guides air suctioned from the outside;

a guide path which extends obliquely upward from the suction path and guides air to the sensing path;

a particle discharge port provided at a lower side of the suction path and configured to discharge particles; and an air discharge port through which air having passed through the sensing path is discharged.

16. The particle sensing device of claim 15, wherein the blower unit is configured to suction air at a first speed and at a second speed faster than the first speed.

17. A particle sensing device comprising:

a sensor including a sensing path through which air passes;

a first suction path which guides air including fine particles into the sensing path in a first direction; and a second suction path which guides air including ultrafine particles into the sensing path in a second direction different from the first direction, wherein the sensor is rotatably installed and is selectively connected to one of the first suction path and the second suction path according to a rotation angle of the sensor.

18. The particle sensing device of claim 17, wherein the second suction path is connected to a flow path which guides air to flow downward, and the second suction path has a portion that extends obliquely upward with respect to the flow path.

19. The particle sensing device of claim 17, further comprising a driving motor which generates a rotation force to rotate the sensor.

20. The particle sensing device of claim 17, wherein the first direction and the second direction form an angle of about 90°; and rotation of the sensor by about 90° causes a section path connected to the sensor to change from one of the first suction path and the second suction path to another of the first suction path and the second suction path.

* * * * *